(12) United States Patent
Bertha et al.

(10) Patent No.: US 8,392,209 B1
(45) Date of Patent: Mar. 5, 2013

(54) SYSTEMS, METHODS, AND APPARATUSES FOR BARCODED SERVICE REQUESTS AND RESPONSES ASSOCIATED WITH HEALTHCARE TRANSACTIONS

(75) Inventors: Brian Bertha, Danville, CA (US); David Weinstein, Danville, CA (US)

(73) Assignee: McKesson Specialty Arizona Inc., Scottsdale, AZ (US)

(*) Notice: Subject to any disclaimer, the term of this patent is extended or adjusted under 35 U.S.C. 154(b) by 119 days.

(21) Appl. No.: 12/814,465

(22) Filed: Jun. 13, 2010

(51) Int. Cl.
*G06Q 50/00* (2012.01)

(52) U.S. Cl. .............................. 705/2; 705/3

(58) Field of Classification Search .............. 705/2, 3
See application file for complete search history.

(56) References Cited

U.S. PATENT DOCUMENTS

| | | | |
|---|---|---|---|
| 4,491,725 A | 1/1985 | Pritchard | |
| 4,674,041 A | 6/1987 | Lemon et al. | |
| 4,723,212 A | 2/1988 | Mindrum et al. | |
| 4,910,672 A | 3/1990 | Off et al. | |
| 5,007,641 A | 4/1991 | Seidman | |
| 5,080,364 A | 1/1992 | Seidman | |
| 5,173,851 A | 12/1992 | Off et al. | |
| 5,201,010 A | 4/1993 | Deaton et al. | |
| 5,237,620 A | 8/1993 | Deaton et al. | |
| 5,305,196 A | 4/1994 | Deaton et al. | |
| 5,327,508 A | 7/1994 | Deaton et al. | |
| 5,388,165 A | 2/1995 | Deaton et al. | |
| 5,430,644 A | 7/1995 | Deaton et al. | |
| 5,448,471 A | 9/1995 | Deaton et al. | |
| 5,588,649 A | 12/1996 | Blumberg et al. | |
| 5,592,560 A | 1/1997 | Deaton et al. | |
| 5,612,868 A | 3/1997 | Off et al. | |
| 5,621,812 A | 4/1997 | Deaton et al. | |
| 5,628,530 A | 5/1997 | Thornton | |
| 5,638,457 A | 6/1997 | Deaton et al. | |

(Continued)

FOREIGN PATENT DOCUMENTS

| | | |
|---|---|---|
| CA | 2482370 A1 | 3/2006 |
| WO | WO 9500569 A3 | 2/1995 |

(Continued)

OTHER PUBLICATIONS

Final Office Action for U.S. Appl. No. 12/186,246 mailed May 9, 2011.

(Continued)

*Primary Examiner* — Neha Patel
(74) *Attorney, Agent, or Firm* — Sutherland Asbill & Brennan LLP

(57) ABSTRACT

Systems, methods, and apparatuses are provided for supporting barcoded service requests and responses. The systems, methods, and apparatuses can support receiving, from a pharmacy computer, a claim request that identifies at least a patient and a prescribed product; determining, based upon the claim request, that a service request is available, the service request indicating an opportunity for one or more services to be provided by the pharmacy to the patient; storing claim information in association with a bar code, the claim information including information from the claim request, the bar code associated with the service request; automatically directing a delivery of the service request to the pharmacy, the service request including the bar code; and receiving a response to the service request, wherein the response includes the bar code, where the bar code is utilized, at least in part, to obtain at least a portion of the claim information for documentation of the one or more provided services.

14 Claims, 8 Drawing Sheets

U.S. PATENT DOCUMENTS

| | | | |
|---|---|---|---|
| 5,642,485 A | 6/1997 | Deaton et al. |
| 5,644,723 A | 7/1997 | Deaton et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,832,457 A | 11/1998 | O'Brien |
| 5,845,255 A | 12/1998 | Mayaud |
| 5,857,175 A | 1/1999 | Day et al. |
| 5,892,827 A | 4/1999 | Beach et al. |
| 5,915,007 A | 6/1999 | Klapka |
| 5,926,795 A | 7/1999 | Williams |
| 5,950,630 A | 9/1999 | Portwood et al. |
| 5,970,469 A | 10/1999 | Scroggie et al. |
| 5,974,399 A | 10/1999 | Giuliani et al. |
| 6,012,035 A | 1/2000 | Freeman, Jr. et al. |
| 6,014,630 A | 1/2000 | Jeacock et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,076,069 A | 6/2000 | Laor |
| 6,094,276 A | 7/2000 | Yamaguchi et al. |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker |
| 6,307,958 B1 | 10/2001 | Deaton et al. |
| 6,321,210 B1 | 11/2001 | O'Brien et al. |
| 6,334,108 B1 | 12/2001 | Deaton et al. |
| 6,351,735 B1 | 2/2002 | Deaton et al. |
| 6,377,935 B1 | 4/2002 | Deaton et al. |
| 6,424,949 B1 | 7/2002 | Deaton et al. |
| 6,484,146 B2 | 11/2002 | Day et al. |
| 6,584,448 B1 | 6/2003 | Laor |
| 6,684,195 B1 | 1/2004 | Deaton et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,885,994 B1 | 4/2005 | Scroggie et al. |
| 7,024,374 B1 | 4/2006 | Day et al. |
| 7,058,584 B2 | 6/2006 | Kosinski et al. |
| 7,058,591 B2 | 6/2006 | Giuliani et al. |
| 7,155,397 B2 | 12/2006 | Alexander et al. |
| 7,225,052 B2 | 5/2007 | Foote et al. |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,415,426 B2 | 8/2008 | Williams et al. |
| 7,426,480 B2 | 9/2008 | Granger et al. |
| 7,720,697 B1 * | 5/2010 | Silverstein ............... 705/3 |
| 2002/0002495 A1 | 1/2002 | Ullman |
| 2002/0032582 A1 | 3/2002 | Feeney et al. |
| 2002/0035484 A1 | 3/2002 | McCormick |
| 2002/0087583 A1 | 7/2002 | Morgan et al. |
| 2002/0111832 A1 | 8/2002 | Judge |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0050802 A1 | 3/2003 | Jay et al. |
| 2003/0069760 A1 | 4/2003 | Gelber |
| 2003/0074218 A1 | 4/2003 | Liff et al. |
| 2003/0074225 A1 * | 4/2003 | Borsand et al. ............. 705/3 |
| 2003/0125986 A1 | 7/2003 | Collosi |
| 2003/0149625 A1 | 8/2003 | Leonardi et al. |
| 2003/0154163 A1 | 8/2003 | Phillips et al. |
| 2003/0229514 A2 | 12/2003 | Brown |
| 2003/0229540 A1 | 12/2003 | Algiene |
| 2004/0039599 A1 | 2/2004 | Fralic |
| 2004/0049422 A1 | 3/2004 | Mortimer |
| 2004/0054657 A1 | 3/2004 | Takeyama |
| 2004/0073457 A1 | 4/2004 | Kalies |
| 2004/0078234 A1 | 4/2004 | Tallal, Jr. et al. |
| 2004/0107117 A1 | 6/2004 | Denny |
| 2004/0111277 A1 | 6/2004 | Pearson et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0220829 A1 | 11/2004 | Baharav et al. |
| 2004/0249745 A1 | 12/2004 | Baaren |
| 2005/0015280 A1 | 1/2005 | Gabel et al. |
| 2005/0033610 A1 | 2/2005 | Cunningham |
| 2005/0060201 A1 | 3/2005 | Connely, III et al. |
| 2005/0086081 A1 | 4/2005 | Brock-Fisher |
| 2005/0090425 A1 | 4/2005 | Reardan et al. |
| 2005/0102169 A1 | 5/2005 | Wilson |
| 2005/0137912 A1 | 6/2005 | Rao et al. |
| 2005/0154627 A1 | 7/2005 | Zuzek et al. |
| 2005/0171815 A1 | 8/2005 | Vanderveen |
| 2005/0187793 A1 | 8/2005 | Myles |
| 2005/0197862 A1 | 9/2005 | Paterson et al. |
| 2005/0222875 A1 | 10/2005 | Lordeman et al. |
| 2005/0222952 A1 | 10/2005 | Garrett et al. |
| 2005/0240473 A1 | 10/2005 | Ayers, Jr. et al. |
| 2005/0288972 A1 | 12/2005 | Marvin et al. |
| 2006/0015518 A1 | 1/2006 | Eletreby et al. |
| 2006/0020514 A1 | 1/2006 | Yered |
| 2006/0026041 A1 | 2/2006 | Ullman |
| 2006/0111941 A1 | 5/2006 | Blom |
| 2006/0149587 A1 | 7/2006 | Hill, Sr. et al. |
| 2006/0149784 A1 | 7/2006 | Tholl et al. |
| 2006/0184391 A1 | 8/2006 | Barre et al. |
| 2006/0224415 A1 | 10/2006 | Hudson et al. |
| 2006/0229915 A1 | 10/2006 | Kosinski et al. |
| 2006/0259330 A1 | 11/2006 | Schranz |
| 2006/0259363 A1 | 11/2006 | Jhetam |
| 2006/0271398 A1 | 11/2006 | Belcastro |
| 2006/0287886 A1 | 12/2006 | Kitazawa |
| 2007/0005402 A1 | 1/2007 | Kennedy et al. |
| 2007/0050209 A1 | 3/2007 | Yered |
| 2007/0088576 A1 | 4/2007 | de Beus et al. |
| 2007/0124177 A1 | 5/2007 | Engleson et al. |
| 2007/0136100 A1 | 6/2007 | Daugherty et al. |
| 2007/0136376 A1 | 6/2007 | Kusakabe |
| 2007/0179957 A1 | 8/2007 | Gibson et al. |
| 2007/0233525 A1 | 10/2007 | Boyle |
| 2007/0233526 A1 * | 10/2007 | Hoffman et al. ............... 705/4 |
| 2007/0239493 A1 | 10/2007 | Sweetland et al. |
| 2008/0103814 A1 | 5/2008 | Fabius et al. |
| 2008/0121688 A1 * | 5/2008 | Harrop ............... 235/375 |
| 2008/0154643 A1 | 6/2008 | Leon |
| 2009/0327363 A1 * | 12/2009 | Cullen et al. ............... 707/204 |
| 2010/0017296 A1 | 1/2010 | Spignesi et al. |

FOREIGN PATENT DOCUMENTS

| | | | |
|---|---|---|---|
| WO | WO 0039737 A1 | 7/2000 |
| WO | WO 2007025295 A2 | 3/2007 |

OTHER PUBLICATIONS

Non-Final Office Action for U.S. Appl. No. 12/186,246 mailed Sep. 1, 2010.

Final Office Action for U.S. Appl. No. 12/565,184 mailed Jan. 31, 2012.

Final Office Action for U.S. Appl. No. 12/415,144 mailed Feb. 13, 2012.

Non-Final Office Action for U.S. Appl. No. 12/725,015 mailed Mar. 19, 2012.

Non-Final Office Action for U.S. Appl. No. 12/725,009 mailed Mar. 14, 2012.

Final Office Action for U.S. Appl. No. 12/649,931 mailed Apr. 3, 2012.

Non-Final Office Action for U.S. Appl. No. 12/414,814 mailed Aug. 18, 2011.

Non-Final Office Action for U.S. Appl. No. 12/415,144 mailed Sep. 19, 2011.

Non-Final Office Action for U.S. Appl. No. 12/540,938 mailed Sep. 29, 2011.

Non-Final Office Action for U.S. Appl. No. 12/565,184 mailed Oct. 4, 2011.

Non-Final Office Action for U.S. Appl. No. 12/649,931 mailed Nov. 9, 2011.

Final Office Action for U.S. Appl. No. 12/414,814 mailed Dec. 7, 2011.

Final Office Action for U.S. Appl. No. 12/540,938 mailed Jan. 19, 2012.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-PRE-SCRIPTIONS, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-32. vol. 63, Issue 1, USA.

Anonymous, TechRx Announces Successful Beta Deployment of T-Rex. PR Newswire. May 13, 2002.

Final Office Action for U.S. Appl. No. 12/725,015 mailed Oct. 11, 2012.

Final Office Action for U.S. Appl. No. 12/725,009 mailed Nov. 21, 2012.

Non-Final Office Action for U.S. Appl. No. 12/414,814 mailed Dec. 5, 2012.

* cited by examiner

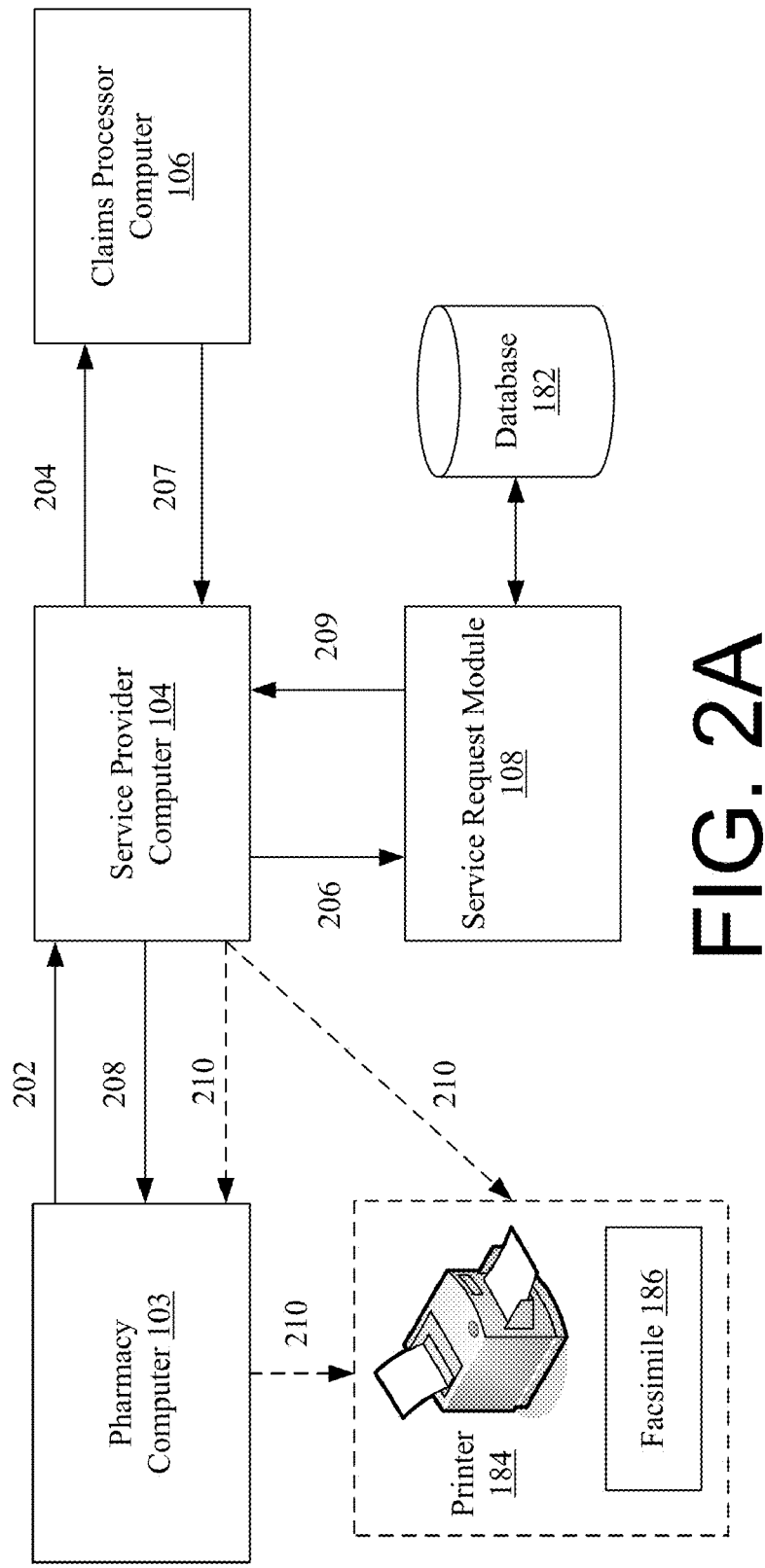

505

Pharmacy Intervention Program
Counseling Opportunity

! PATIENT ARRIVING SOON / ATTACH FAX TO RX !

[Patient Name]  
[Patient DOB / Patient Sex]  
[Pharmacy Name or ID]  
[Prescription (Rx) Number]

<u>Intervention:</u>  
[Product Name] First Refill  
Date of Rx Claim: MM/DD/YYYY  
Intervention Fee: $X.00

---

[Product Name] First Refill Consultation

PLEASE ALERT PHARMACIST this prescription is eligible for adherence counseling through the Pharmacy Intervention Program (PIP)

Perform the following steps to complete the consult:

1 25002 74135 0

1. Attach this fax to the will call prescription listed above.
2. Perform adherence consultation using intervention guides and brand-specific patient materials.
3. Save this fax as a reminder for billing.
4. Billing—sign and fax this form to (123) 456-7890 to submit claim.

*I have delivered the adherence consultation described on this form.*

Pharmacist Signature_____ Date_____

Pharmacy Intervention Program
Counseling Opportunity

! PATIENT ARRIVING SOON / ATTACH FAX TO RX !

Patient:
John Doe
DOB: MM/DD/YYYY Male
Pharmacy: Joe's Pharmacy
RX#: 2491912354

Intervention:
[Product Name] First Refill
Date of Rx Claim: DD-MM-YYYY 14:28EST
Intervention Fee: $XX.00

[Product Name] First Refill Consultation

*Pharmacist:* Please deliver consultation according to PIP program guidelines and answer the assessment questions below by placing an "X" as appropriate:

Patient Assessment

| Question | | |
|---|---|---|
| Prior to the consult, did the patient have a clear understanding of the therapeutic benefits of the medication? | ☐ Yes | ☐ No |
| Prior to the consult, did the patient have a clear understanding of the approximate duration of therapy for the medication? | ☐ Yes | ☐ No |
| Does the patient believe a reminder system would help improve his/her adherence? | ☐ Yes | ☐ No |
| If the answer is "yes" to the previous question, which channel or channels does the patient prefer? | ☐ IVR ☐ email | ☐ Text ☐ Letter |

Billing—sign and fax this form to (866) 680-4702 to submit claim.

*I have delivered the adherence consultation described on this form.*

Pharmacist Signature_____ Date _____

*If you have received this transmission in error or for more information, questions or to request replacement materials, please call [Service Provider] at 1-866-123-4567. Program information is also available at [website address].*

FIG. 5B

SYSTEMS, METHODS, AND APPARATUSES FOR BARCODED SERVICE REQUESTS AND RESPONSES ASSOCIATED WITH HEALTHCARE TRANSACTIONS

FIELD OF THE INVENTION

Aspects of the invention relate generally to barcoded service requests and responses associated with healthcare transactions.

BACKGROUND OF THE INVENTION

Year over year increases in healthcare costs in the United States have outstripped general inflation for years. It has become clear that to successfully produce quality health outcomes for the public at large at sustainable costs, the patient must be an active player in decision making and adapt optimal behaviors consistent with achieving those outcomes. Finding cost-effective methods to successfully engage consumers to change their health-related behaviors has proven to be difficult.

Prior solutions have attempted to utilize pharmacists to counsel patients to achieve quality health outcomes. However, these prior solutions utilized solutions that are outside of typical pharmacy workflows. As such, compliance by pharmacists has been minimal. Accordingly, there is an opportunity in the industry for systems, methods, and apparatuses for barcoded service requests and responses associated with healthcare transactions.

SUMMARY OF THE INVENTION

Some or all of the above needs and/or problems may be addressed by certain embodiments of the invention. Embodiments of the invention may include systems, methods, and apparatuses for barcoded service requests and responses associated with healthcare transactions. According to an example embodiment of the invention, there is a method. The method may include determining, based at least in part on the identified drug or product in the prescription claim request, that a service request is available, the service request indicating an opportunity for one or more services to be provided by the pharmacy to the patient; storing prescription claim information in association with a bar code, the prescription claim information including information from the prescription claim request, the bar code associated with the service request; automatically directing, responsive to the determination that the service request is available, a delivery of the service request to the pharmacy, the service request including the bar code; receiving a response to the service request, wherein the response includes the bar code, wherein the bar code is utilized, at least in part, to obtain at least a portion of the prescription claim information for documentation of the one or more services provided by the pharmacy to the patient. One or more of the prior steps can be performed by one or more computers associated with a service provider.

According to another example embodiment, there is a system. The system may include at least one memory for storing computer-executable instructions, and at least one processor configured to access the memory. The at least one processor can also be configured to execute the computer-executable instructions to: receive a prescription claim request from a pharmacy computer associated with a pharmacy, where the prescription claim request identifies at least a patient, and a prescribed drug or product for the patient; determine, based at least in part on the identified drug or product in the prescription claim request, that a service request is available, the service request indicating an opportunity for one or more services to be provided by the pharmacy to the patient; store prescription claim information in association with a bar code, the prescription claim information including information from the prescription claim request, the bar code associated with the service request; automatically direct, responsive to the determination that the service request is available, a delivery of the service request to the pharmacy, the service request including the bar code, where a response to the service request is received, wherein the response includes the bar code, wherein the bar code is utilized, at least in part, to obtain at least a portion of the prescription claim information for documentation of the one or more services provided by the pharmacy to the patient.

BRIEF DESCRIPTION OF THE DRAWINGS

Reference will now be made to the accompanying drawings, which are not necessarily drawn to scale, and wherein:

FIG. 2A illustrates an example block diagram for delivering a barcoded service request based upon one or more healthcare transactions, according to an example embodiment of the invention.

FIGS. 5A-5C illustrate example illustrations of service requests in accordance with example embodiments of the invention.

DETAILED DESCRIPTION

Figure 1:
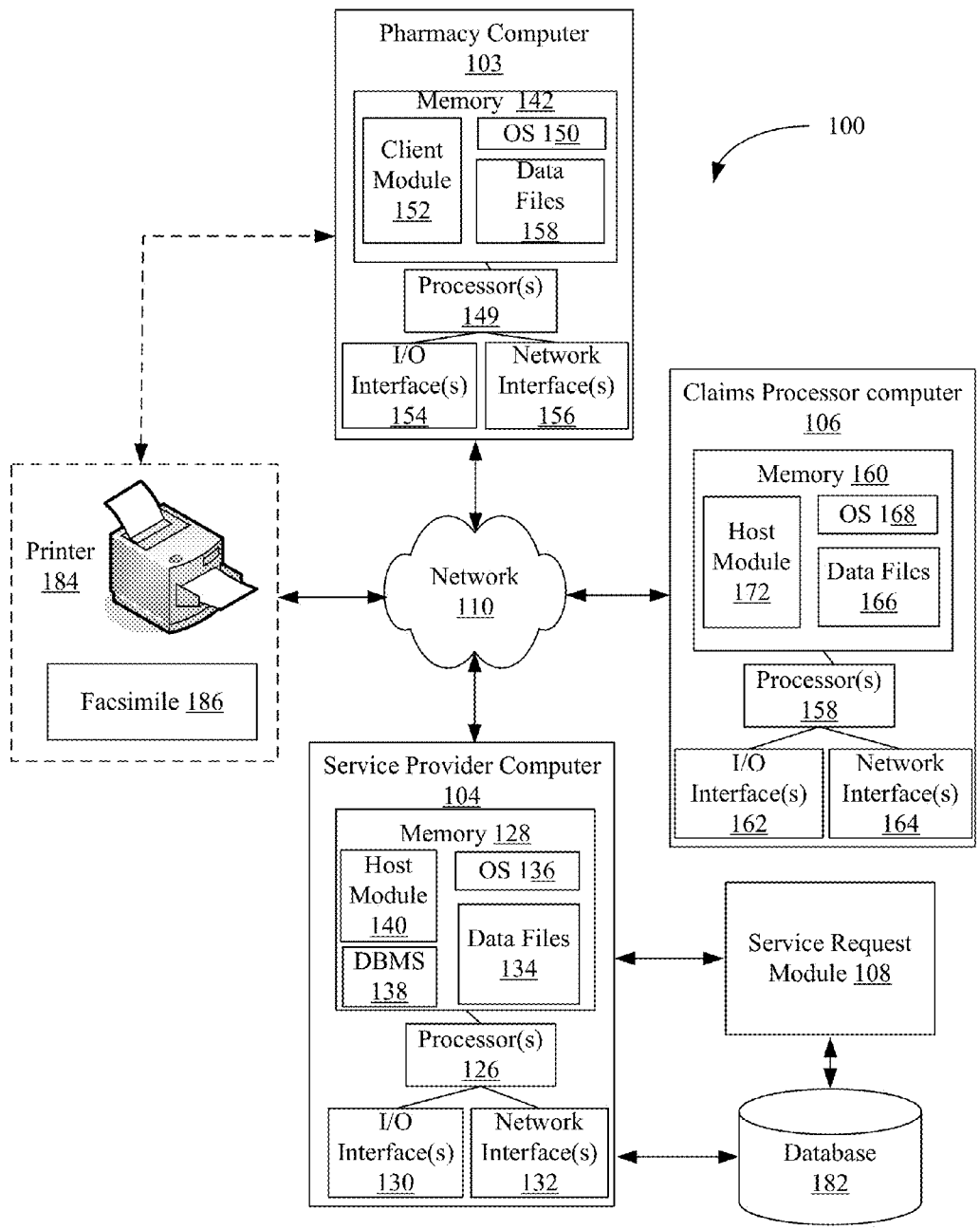
FIG. 1 illustrates an example healthcare system for supporting barcoded service requests and responses associated with a healthcare transaction, according to an example embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention can provide systems, methods, and apparatuses for barcoded service requests associated with healthcare transactions. In an example embodiment of the invention, a service request can be generated by a service provider based upon the processing of a received healthcare transaction such as a prescription claim transaction. The service request can include a bar code to facilitate later identification of the service request, as well as information in the corresponding healthcare transaction (e.g., prescription claim transaction). The barcoded service request can be delivered to a recipient, such as a pharmacist/pharmacy or other healthcare provider (e.g., doctor, nurse practitioner), although other recipients are available, including a patient or caregiver. The delivery of the barcoded service request can be delivered to the recipient via facsimile or printer. However, in other example embodiments of the invention, the barcoded service request can also be delivered via many other types of electronic communications such as by e-mail or as an electronic file without departing from example embodiments of the invention.

A recipient, such as a pharmacist/pharmacy or other healthcare provider, can then follow the specified directions or instructions provided by the barcoded service request. For example, the barcoded service request can direct or instruct a pharmacist/pharmacy or other healthcare provider to provide one or more services to a particular patient, according to an example embodiment of the invention. These services can include counseling the patient in accordance with one or more healthcare programs such as, but not limited to, pharmacy intervention programs (PIP), medication therapy management (MTM) programs, or loyalty programs. Upon completion of providing the services to the patient, the pharmacist/pharmacy or other healthcare provider returns a copy of the barcoded service request to the service provider. The copy of the barcoded service request can be returned via facsimile, although other electronic communications can be utilized without departing from example embodiments of the invention. It will be appreciated that even when the copy of the barcoded service request is returned by facsimile, the service provider can receive the copy in an electronic format (e.g., a file). It will also be appreciated that in some example embodiments, the barcoded service request can also include one or more data collection fields. Accordingly, the pharmacist or other healthcare provider can provide one or more values for the data collection fields prior to returning the copy of the barcoded service request to the service provider. As such, the returned copy of the barcoded service request can serve as a response to the delivered service request.

Upon receipt of the response, the service provider can scan the barcode to use the obtained bar code information to identify at least a portion of the healthcare transaction information that was associated with the service request. Indeed, the bar code, or information associated with the bar code, may have been previously stored in conjunction with the healthcare transaction information to facilitate later retrieval of the healthcare transaction information. The obtained portion of the healthcare transaction information can be used in documenting the one or more services provided by the pharmacist/pharmacy or other healthcare provider to the patient. Likewise, in some example embodiments, the response can further include one or more respective values for any data collection fields. Optical mark recognition, which may include optical character recognition, can be used to obtain the values for the data collection fields, and these values can be used or stored when documenting the one or more services provided by the pharmacist/pharmacy or other healthcare provider to the patient. The documentation of the one or more services provided by the pharmacy to the patient can also be used for facilitating or completing patient enrollment in one or more healthcare programs. In addition to documenting services, the obtained prescription claim information can also be utilized to facilitate billing for the one or more services provided to the patient by the pharmacy/pharmacist. Indeed, a pharmacy may be compensated for providing one or more services to a patient in accordance with a service request. Funding to compensate the pharmacy may be obtained from a sponsor of the service request, which may include a pharmaceutical manufacturer/distributor, a health plan sponsor, an insurance company, or another healthcare provider.

The term "product," and its pluralized form, as used herein, is intended to refer to any good, including a drug or other substance.

System Overview

An example healthcare system 100 for supporting barcoded service requests and responses associated with a healthcare transaction will now be described illustratively with respect to FIG. 1. As shown in FIG. 1, the system 100 may include a pharmacy computer 103, a service provider computer 104, and a claims processor computer 106, which are each configured for accessing and reading associated computer-readable media having stored thereon data and/or computer-executable instructions for implementing the various methods of the invention. Generally, network devices and systems, including the one or more pharmacy computers 103, service provider computers 104, and claims processor computers 106 have hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. By executing computer-executable instructions, each of the network devices may form a special purpose computer or particular machine. As used herein, the term "computer-readable medium" may describe any form of memory or memory device.

As shown in FIG. 1, the one or more pharmacy computers 103, service provider computers 104, and claims processor computers 106 may be in communication with each other via a network 110, which as described below can include one or more separate or shared private and public networks, including the Internet or a publicly switched telephone network. Each of these components—the pharmacy computer 103, the service provider computer 104, the claims processor computer 106, and the network 110—will now be discussed in further detail.

First, the pharmacy computer 103 may be associated with one or more pharmacies, including a retail pharmacy or pharmacy group, according to an example embodiment of the invention. The pharmacy computer 103 may be any processor-driven device, such as a desktop computer, laptop computer, handheld computer, and the like. In addition to having processor(s) 149, the pharmacy computer 103 may further include a memory 142, input/output ("I/O") interface(s) 154, and network interface(s) 156. The memory 142 may store data files 158 and various program modules, such as an operating system ("OS") 150 and a client module 152. The memory 142 may be any computer-readable medium, coupled to the processor 149, such as RAM, ROM, and/or a removable storage device for storing data files 158 and a database management system ("DBMS") to facilitate management of data files 158 and other data stored in the memory 142 and/or stored in separate databases. The OS 150 may be, but is not limited to, Microsoft Windows®, Apple OSX™, Unix, or a mainframe operating system. The client module 152 may be an Internet browser or other software, including a dedicated program, for interacting with a physician/healthcare provider computer (not shown), the service provider computer 104, and/or the claims processor computer 106. For example, a user such as a pharmacist or other pharmacy employee may utilize the client module 152 to receive or retrieve an electronic prescription order from a physician/healthcare provider computer. Likewise, the pharmacist or other pharmacy employee may also utilize the client module 152 in preparing and providing a prescription claim to the service provider computer 104 for delivery to the appropriate claims processor computer 106. The pharmacy computer 103 may also utilize the client module 152 to retrieve or otherwise receive data or responses from the service provider computer 104.

Still referring to the pharmacy computer 103, the I/O interface(s) 154 may facilitate communication between the processor 149 and various I/O devices, such as a keyboard, mouse, printer, microphone, speaker, monitor, bar code readers/scanners, RFID readers, and the like. The network interface(s) 156 may take any of a number of forms, such as a network interface card, a modem, a wireless network card, and the like. It will be appreciated that while the pharmacy computer 103 has been illustrated as a single computer or processor, the pharmacy computer 103 may be comprised of a group of computers or processors, according to an example embodiment of the invention.

The service provider computer 104 includes, but is not limited to, any processor-driven device that is configured for receiving, processing, and fulfilling requests from a physician/healthcare provider computer, the pharmacy computer 103, and/or the claims processor computer 106, relating to prescription, pharmacy, benefits, and/or claims transactions or other activities. According to an example embodiment of the invention, the service provider computer 104 may comprise, but is not limited to, one or more "switches" or "switch providers" performing routing and processing of prescription transactions between covered entities/healthcare providers, pharmacies, payors/claims processors, financial institutions, and/or other service providers.

The service provider computer 104 may include a processor 126, a memory 128, input/output ("I/O") interface(s) 130, and a network interface 132. The memory 128 may be any computer-readable medium, coupled to the processor 126, such as RAM, ROM, and/or a removable storage device for storing data files 134 and a database management system ("DBMS") 138 to facilitate management of data files 134 and other data stored in the memory 128 and/or stored in one or more databases 182. The memory 128 may store data files 134 and various program modules, such as an operating system ("OS") 136, a database management system ("DBMS") 138, and the host module 140. The OS 136 may be, but is not limited to, Microsoft Windows®, Apple OSX™, Unix, or a mainframe operating system.

The data files 134 may also store routing tables for determining the destination of communications received from the pharmacy computer 103, or claims processor computer 106. The host module 140 may receive, process, and respond to requests from the respective client module 152 of the pharmacy computer 103, and may further receive, process, and respond to requests from the host module 172 of the claims processor computer 106. The database 182 may be one or more databases operable for storing pharmacy data and/or information associated with determining or inferring conditions or diseases (or categories associated therewith) from pharmacy data, as described herein.

As also illustrated in FIG. 1, the service provider computer 104 may include or otherwise be in communication with a service request module 108. The service request module 108 may include business rules, perhaps stored in a database 182, for determining whether one or more service requests are relevant or applicable to a particular healthcare transaction received by the service provider computer 104. If the service request module 108 determines that one or more service requests are available, a bar code may be generated for identifying the service request and healthcare transaction information associated with the service request. The service request module 108, either alone or in conjunction with the service provider computer 104, may direct the transmission of the one or more barcoded service requests to a printer 184 or facsimile 186, which may be at or near a location of a healthcare provider (e.g., pharmacy/pharmacist). However, it will be appreciated that the printer 184 or facsimile 186 may also be at another location associated with another individual or recipient (e.g., the patient) without departing from example embodiments of the invention. The transmission from the service request module 108 to the printer 184 or facsimile 186 may be accomplished via any number of suitable networks, for example, a publicly switched telephone network (PSTN), a local area network, a wide area network, a cellular network, a wireless network, the Internet, or another similar network.

In addition, the service request module 108 may receive a response to the barcoded service request. In an example embodiment of the invention, the response may be a returned copy of the service request, and thus, may also include the bar code. The response may also include data values for one or more data collection fields present in the response. Accordingly, optical mark recognition can be used to obtain the bar code information as well as one or more data values for the data collection fields. The service request module 108 may be operative to store a documentation record for the one or more services provided, as indicated by the response. The documentation record, which may be stored in database 182, can include the healthcare transaction information identified from the bar code information, as well as one or more data values obtained from the data collection fields of the response. In some example embodiments, the documentation can also be utilized as part of an enrollment process for one or more healthcare programs. Likewise, the obtained healthcare information can be utilized to facilitate billing for one or more services provided by the pharmacist/pharmacy to the patient.

The service request module 108 may be implemented as computer-implemented instructions of the memory 128 of the service provider computer 104. Alternatively, the service request module 108 may also be implemented as computer-implemented instructions of a memory of a separate processor-based system that operates in tandem with the service provider computer 104, according to an example embodiment of the invention. It will be appreciated that while the service provider computer 104 has been illustrated as a single computer or processor, the service provider computer 104 may be comprised of a group of computers or processors, according to an example embodiment of the invention.

The claims processor computer 106 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The claims processor computer 106 may include a processor 158, a memory 160, input/output ("I/O") interface(s) 162, and a network interface 164. The memory 160 may be any computer-readable medium, coupled to the processor 158, such as RAM, ROM, and/or a removable storage device. The memory 160 may store data files 166 and various program modules, such as an operating system ("OS") 168, a database management system ("DBMS"), and a host module 172. The OS 168 may be, but is not limited to, Microsoft Windows®, Apple OSX™, Unix, or a mainframe operating system. The host module 172 may receive, process, and respond to requests from the client module 152 of the pharmacy computer 103, and may further receive, process, and respond to requests from the host module 140 of the service provider computer 104. According to an example embodiment of the invention, the claims processor computer 106 may be associated with benefits determination by a discount program, an insurance company, a pharmacy benefits manager (PBM), a government payor, or another third-party payor. According to an alternative example embodiment of the invention, a claims processor computer 106 may also be implemented as part of a service provider computer 104.

Still referring to the claims processor computer 106, the I/O interface(s) 162 may facilitate communication between the processor 158 and various I/O devices, such as a keyboard, mouse, printer, microphone, speaker, monitor, bar code readers/scanners, RFID readers, and the like. The network interface 164 may take any of a number of forms, such as a network interface card, a modem, a wireless network card, and the like. It will be appreciated that while the claims processor computer 106 has been illustrated as a single computer or processor, the claims processor computer 106 may be comprised of a group of computers or processors, according to an example embodiment of the invention.

The network 110 may include any telecommunication and/or data network, whether public, private, or a combination thereof, including a local area network, a wide area network, an intranet, an internet, the Internet, intermediate hand-held data transfer devices, a publicly switched telephone network (PSTN), and/or any combination thereof and may be wired and/or wireless. The network 110 may also allow for real-time, off-line, and/or batch transactions to be transmitted between or among the pharmacy computer 103, and/or the service provider computer 104. Due to network connectivity, various methodologies as described herein may be practiced in the context of distributed computing environments. It will also be appreciated that the network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer 104 may form the basis of network 110 that interconnects the pharmacy computer 103 with the claims processor computer 106.

Generally, each of the memories and data storage devices, such as the memories 142, 128, 160 and the database 182, and/or any other memory and data storage device, can store data and information for subsequent retrieval. In this manner, the system 100 can store various received or collected information in memory or in a database associated with one or more pharmacy computers 103, service provider computers 104, and/or claims processor computers 106. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage device. In other embodiments, the databases shown can be integrated or distributed into any number of databases or other data storage devices. In one example embodiment, for security, the service provider computer 104 (or any other entity) may have a dedicated connection to the database 182, as shown; though, in other embodiments, the service provider computer 104 or another entity may communicate with the database 182 via a network 110.

Suitable processors, such as the processors 149, 126, 158 of the pharmacy computer 103, service provider computer 104, and/or claims processor computer 106, respectively, may comprise a microprocessor, an ASIC, and/or a state machine. Example processors can be those provided by Intel Corporation (Santa Clara, Calif.), AMD Corporation (Sunnyvale, Calif.), and Motorola Corporation (Schaumburg, Ill.). Such processors comprise, or may be in communication with media, for example computer-readable media, which stores instructions that, when executed by the processor, cause the processor to perform the elements described herein. Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript. Furthermore, any of the processors may operate any operating system capable of supporting locally executed applications, client-server based applications, and/or browser or browser-enabled applications.

The system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. As an example, in one example embodiment, the service provider computer 104 (or the claims processor computer 106) may be implemented as a specialized processing machine that includes hardware and/or software for performing the methods described herein. In addition, the processor and/or processing capabilities of the service provider computer 104 and/or the service request module 108, may be implemented as part of the pharmacy computer 103, the claims processor computer 106, or any combination or portion thereof. Accordingly, embodiments of the invention should not be construed as being limited to any particular operating environment, system architecture, or device configuration.

Operational Overview

Figure 2B:
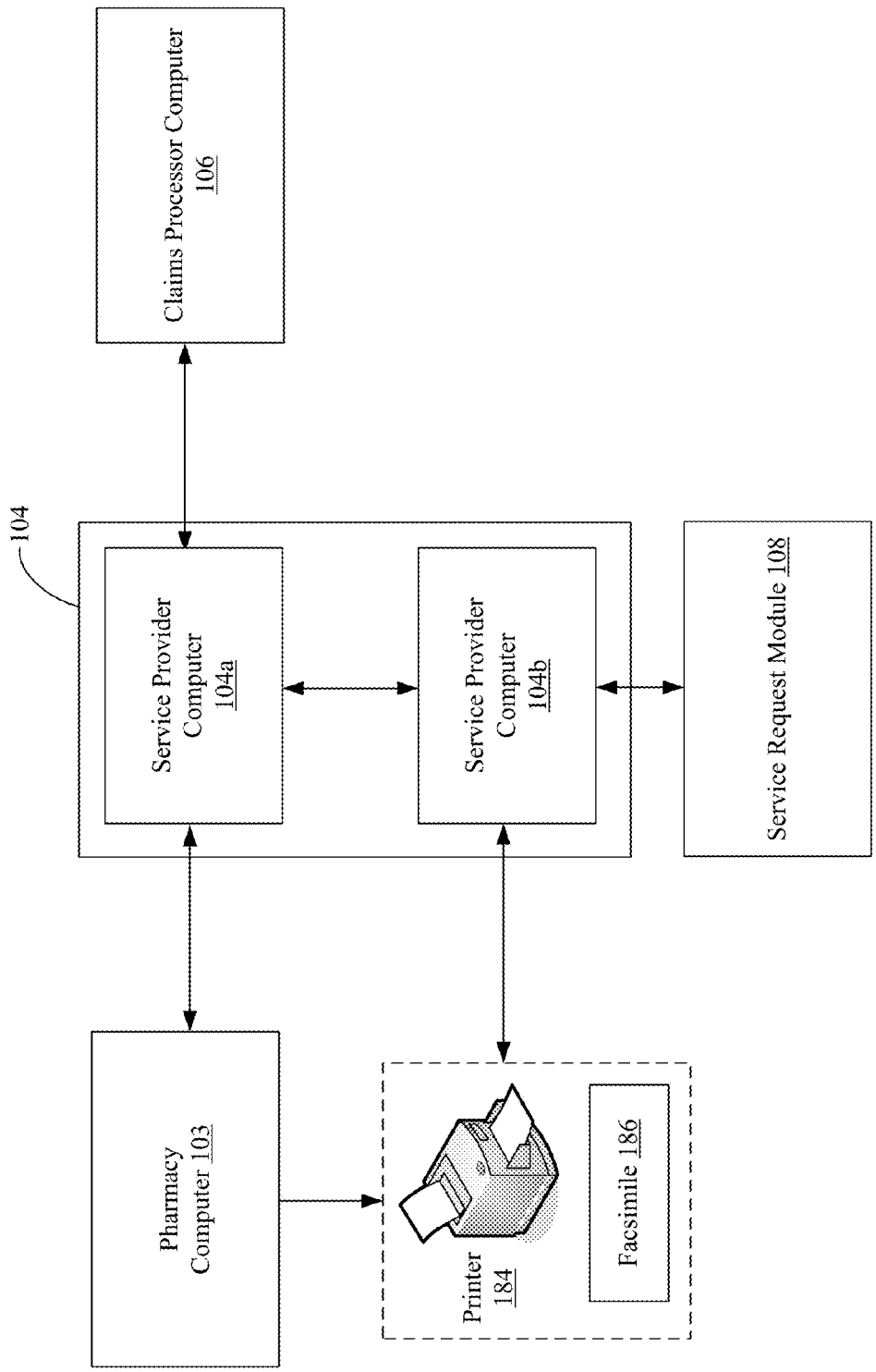
FIG. 2B illustrates an alternative embodiment of the block diagram of FIG. 2A, according to an example embodiment of the invention.
Figure 3:
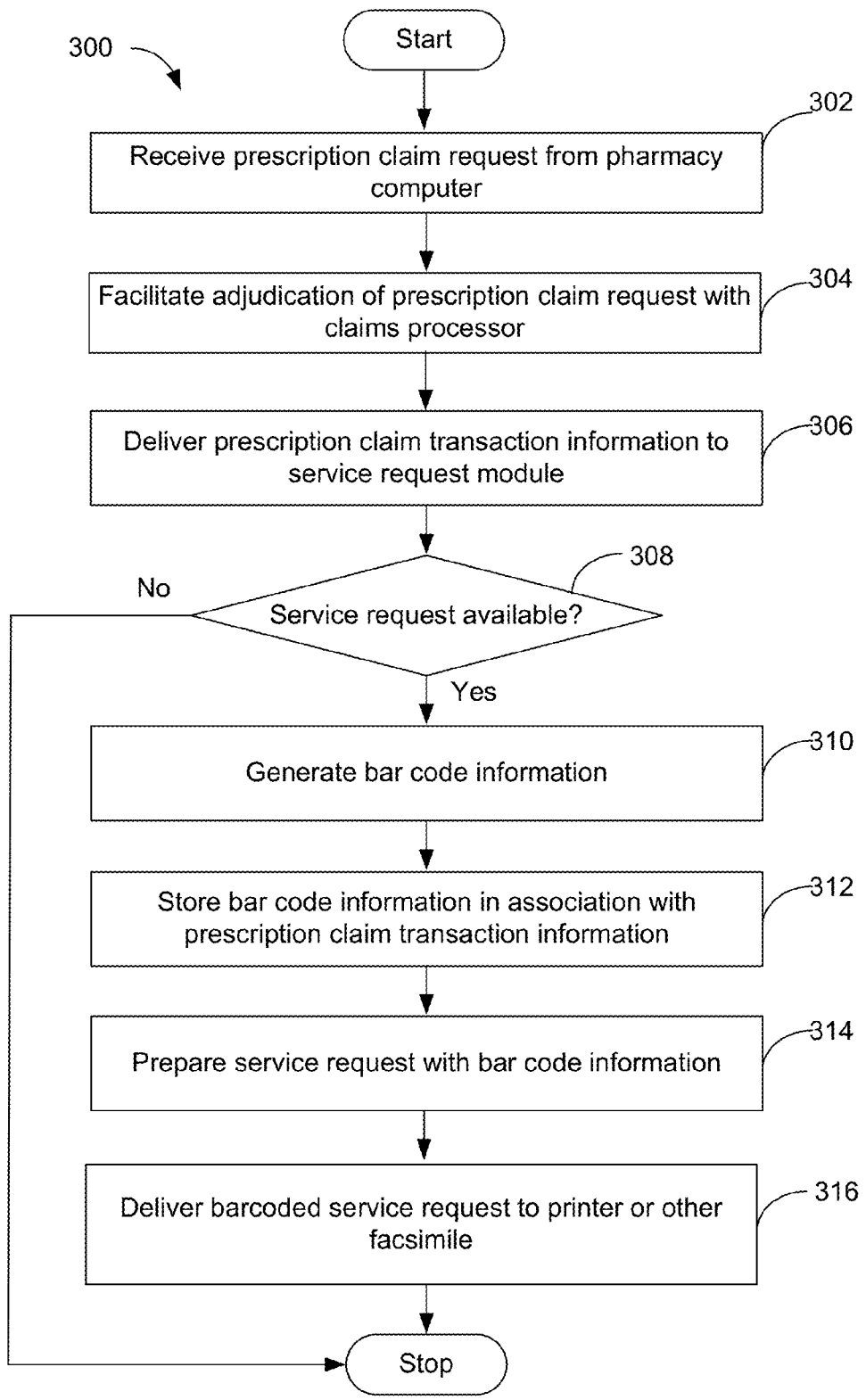
FIG. 3 illustrates an example flow diagram for delivering a barcoded service request based upon one or more healthcare transactions, according to an example embodiment of the invention.

FIGS. 2A and 3 illustrate a respective block diagram and flow diagram for delivering a barcoded service request based upon one or more healthcare transactions, according to an example embodiment of the invention.

Referring now to FIGS. 2A and 3, in block 302, a pharmacy computer 103 may deliver or otherwise communicate a healthcare transaction request in the form of a prescription claim request 202 to the service provider computer 104. Accordingly, the service provider computer 104 may receive the prescription claim request 202 at block 302. The prescription claim request 202 may be in accordance with a version of a National Council for Prescription Drug Programs (NCPDP) Telecommunication Standard, although other standards may be utilized as well. The prescription claim request 202 may include a BIN Number and/or a combination of a BIN Number and Processor Control Number (PCN) for identifying a particular claims processor computer or payor, such as the claims processor computer 106, as a destination for the prescription claim request 202. In addition, the prescription claim request 202 may also include information relating to the patient, payor, prescriber, healthcare provider, and/or the prescribed or administered drug or product. As an example, the prescription claim request 202 received by the service provider computer 104 may include one or more combinations of the following information:

Payer ID/Routing Information for each identified payor or potential payor
- BIN Number and Processor Control Number (PCN) that designates an intended destination of the prescription claim request 202

Patient Information
- Name (e.g., Patient Last Name, Patient First Name, etc.)
- Date of Birth of Patient
- Age of Patient
- Gender
- Patient Address (e.g., Street Address, Zip Code, etc.)
- Patient Contact Information (e.g., Patient Telephone Number)
- Patient ID or other identifier Insurance/Coverage Information
- Cardholder Name (e.g., Cardholder First Name, Cardholder Last Name)
- Cardholder ID and/or other identifier (e.g., person code)

Provider (e.g., Prescriber, Pharmacy) Information
- Prescriber Information
- Primary Care Provider ID or other identifier (e.g., National Provider Identifier (NPI) code)
- Primary Care Provider Name (e.g., Last Name, First Name)
- Prescriber ID or other identifier (e.g., NPI code, Drug Enforcement Administration (DEA) number)
- Prescriber Name (e.g., Last Name, First Name)
- Prescriber Contact Information (e.g., Telephone Number)
- Pharmacy or other Healthcare Provider Information (e.g., store name, chain identifier, etc.)
- Pharmacy or other Healthcare Provider ID (e.g., NPI code)

Claim Information
- Drug or product information (e.g., National Drug Code (NDC))
- Prescription/Service Reference Number
- Date Prescription Written
- Quantity Dispensed
- Number of Days Supply
- Diagnosis/Condition
- Pricing information for the drug or product (e.g., network price, Usual & Customary price)
- Date of Service.

It is appreciated that the aforementioned information is provided for illustrative purposes, and that any number of fields can be included in a prescription claim request 202 as desired or required. Moreover, one or more of the aforementioned fields may be stored locally by the service provider computer 104, such as in a database 182, and be retrieved based on a unique identifier (or combination of information) transmitted in the prescription claim request 202.

At block 304, the service provider computer 104 may facilitate adjudication of the prescription claim request 202 with a claims processor computer 106. To do so, the service provider computer 104 may determine the destination claims processor computer 106 based upon a BIN/PCN included with the prescription claim request 202. The service provider computer 104 may then route or deliver a copy of prescription claim request 202 to the destination claims processor computer 106 as prescription claim request 204 for coverage or benefits determination by a discount program, insurance company, pharmacy benefits manager (PBM), government payor, or another third-party payor. Where the claims processor computer 106 is implemented as part of the service provider computer 104, the delivery of the prescription claim request 204 may be an internal delivery or intra-network delivery. However, where the claims processor computer 106 is distinct from the service provider computer 104, the delivery of the prescription claim request 204 may be an external delivery or inter-network delivery, perhaps via a network 110, according to an example embodiment of the invention. The claims processor computer 106 may then adjudicate the prescription claim request 204 and generate a claim response 207. The claim response 207 may specify a covered amount (e.g., an insured amount) and a patient-responsible amount (e.g., a co-pay or coinsurance amount). Alternatively, the claim response 207 may indicate a denial of coverage for the prescription claim request 204. The claims processor computer 106 may then deliver the claim response 207, which is received by the service provider computer 104. The claim response 207 may also be provided to the pharmacy computer 103 as claim response 208.

At block 306, the service provider computer 104 may also deliver a copy of the prescription claim request 202 and/or claim response 207, which comprise the prescription claim transaction information, to the service request module 108 in one or more messages 206. For multiple deliveries, the service provider may have initially provided a copy of the prescription claim request 202 according to a first delivery at a first time, and then provided a copy of the claim response 207 according to a second delivery at a second time. Where the service request module 108 is part of the service provider computer 104, the delivery of the one or more messages 206 may be an internal delivery or an intra-network delivery. However, where the service request module 108 is distinct from the service provider computer 104, then the delivery of the one or more messages 206 may be an external delivery or inter-network delivery, perhaps via a network 110, according to an example embodiment of the invention.

Still referring to block 306, the service request module 108 may parse or examine the copy of the prescription claim request 202 and/or claim response 207 received in the one or more messages 206 to obtain transaction information for use in determining availability of one or more service requests for delivery. The information that may be obtained from the prescription claim request 202 and/or claim response 207 may include an identification of the prescribed drug/product (e.g., a drug or product identifier such as an NDC), the patient, the pharmacy, or an indication of whether the prescription claim request 204 was approved or denied for coverage.

At block 308, the service request module 108 may determine whether one or more service requests may be available based upon the information obtained from the prescription claim request transaction, either alone or in conjunction with other information such as past prescription claim transaction history for patients. Different business rules may be available at block 308 depending upon the qualification criteria of the service request. Examples of these business rules may include one or more combinations of the following:

Whether the patient is qualified based upon patient information included in or derived from patient information. For example, a service request may be available for patients of a particular age (or within an age range), gender, location (e.g., by city, state, or zip code).

Whether the prescribed drug or product (e.g., by NDC) identified in the current prescription claim transaction is a qualified drug or product. As an example, a pharmaceutical manufacturer or other healthcare provider may sponsor one or more service requests for certain ones of its drugs or products. As such, a service request may be available if the prescription claim information indicates an NDC of a qualified drug or product.

Whether the patient has (or has not) taken one or more drugs or products, either concurrently or previously. Indeed, the business rules may determine, based upon stored patient transaction history (e.g., previously adjudicated prescription claim transactions) in database 182, whether the patient has (or has not) taken one or more drugs or products, or classes of drugs or products within a predetermined time period (e.g., past 3 months, 6 months, etc.).

a. A first example is whether the patient is (or is not) "New to Therapy" for the particular drug or product (or class of drug or product) identified in the current prescription claim transaction. As an example, the business rules may determine, based upon stored patient transaction history in database 182, whether the patient has taken the same drug or product (as identified in the current prescription claim transaction), or same class of the drug or product, within a predetermined period of time (e.g., past 3 months, 6 months, etc.). A service request may be available for a patient who is new to therapy for a particular drug or product. However, another service request may be available for those not new to therapy as well.

b. A second example is whether the patient is (or is not) utilizing another drug or product (or class of drug or product) than that identified in the current prescription claim transaction. As an example, the business rules may determine, based upon stored patient transaction history in database 182, whether the patient has taken another drug or product (or class of drug or product) within a predetermined period of time (e.g., past 3 months, 6 months, etc.). A service request may be available for a patient that has (or has not) taken one or more other drugs.

Whether the prescription claim request was denied coverage by the claims processor computer. A denied prescription claim request may result in a service request not being made available.

Whether the pharmacy identified in the prescription claim transaction is a qualified pharmacy. A service request may be available for qualified pharmacies that wish to receive service requests. As an example, a qualified pharmacy can be determined by matching an NPI number or other Pharmacy Identification Number in the current prescription claim request transaction to corresponding information in an eligible pharmacy list, as illustrated by Table I below, which may represent one or more records stored in database 182.

TABLE I

| Pharmacy Identification Information (e.g., NPI or DEA) | Pharmacy Contact Information (e.g., address, phone number) | Delivery Type | Destination ID |
|---|---|---|---|
| NPI # 1 | Address & Phone Number | Facsimile | Fax Number |
| NPI # 2 | Address & Phone Number | Printer | Printer ID |
| ... | ... | ... | ... |

As shown in Table I, the illustrative eligible pharmacy list may provide a Delivery Type and/or Destination ID for determining how any available service request may be delivered to the printer 184 or facsimile 186. For example, a fax number may be provided if one or more service requests are to be delivered by facsimile 186. Likewise, a printer ID (e.g., IP Address, MAC ID, or network address) that identifies a particular printer 184 may be provided if the one or more available service requests are to be delivered over a network (e.g., wireless or cellular network) to the printer 186, either directly or via pharmacy computer 103. Many other variations of the eligible provider list are available without departing from example embodiments of the invention. For example, if the recipient is not a pharmacy or pharmacist, then Table I can include entries for other recipients such as for patients (e.g., based upon Cardholder ID), doctors (e.g., by Provider ID), or other healthcare providers.

If block 308 determines that one or more service requests are available, then processing may proceed to block 310. At block 310, the service request module may generate a bar code, which may be utilized to identify a particular available service request, which may indicate one or more opportunities for services for the patient. At block 312, the bar code generated in block 310, or information associated with the bar code, may likewise be stored, perhaps in a record of database 182, in association with the claim transaction information that was received in a message 206. As such, the bar code, or information associated with the bar code, may likewise be used to identify the corresponding prescription claim transaction information, perhaps when one or more services have been provided by the pharmacy to the patient, or for billing purposes associated with services provided by the pharmacy or patient.

At block 314, one or more available service requests may be coded with the bar code generated at block 310. In an example embodiment of the invention, block 314 may utilize a template for one or more service requests, where the template provides a preferred formatting for the service requests and has one or more predefined locations for the bar code. The template may likewise include one or more sections for inclusion of one or more data collection fields. These data collection fields may be used to request healthcare data values from a recipient to facilitate completion or documentation of one or more of the requested services. For example, the data collection fields may be used to assess patient understanding during a consultation, or obtain healthcare information (e.g., conditions, smoking status, etc.) from the patient. It will be appreciated that many other variations of the service request may be available without departing from example embodiments of the invention. According to an example embodiment of the invention, the service requests may be sponsored or otherwise originated by a healthcare provider, a pharmacy, a pharmaceutical manufacturer/distributor, a service provider, or yet another entity. It will be appreciated that the sponsors of the service request may pay a fee to a service provider that promotes or distributes the service request, according to an example embodiment of the invention. Likewise, the service provider may pay a fee to a pharmacy or other recipient (e.g., doctor) for completing one or more services requested by the service request, according to an example embodiment of the invention.

At block 316, the service request module 108 can deliver a response 209 to the service provider computer 104, where the response includes the one or more barcoded service requests. The service provider computer 104 may then deliver or direct the delivery of a message 210 with the barcoded service request to the printer 184 or facsimile 186. In an example embodiment of the invention, the service provider computer 104 may direct the delivery of the message 210 with the barcoded service request to the printer 184 or facsimile 186 via one or more networks, including the Internet, a cellular network, or other wireless network. Another entity (e.g., associated with a patient information exchange) may be utilized by the service provider computer 104 to deliver the message 210 to the printer 184 or facsimile 186.

As an example, the message 210 having the barcoded service request may be delivered by the service provider computer 104 directly to the printer 184 or facsimile 186 without first being received by the pharmacy computer 103. According to another example, the message 210 having the available barcoded service request may be delivered from the service provider computer 104 to the pharmacy computer 103, which in turn may deliver the message 210 having the available service request to the printer 184 or facsimile 186. In an optional example embodiment of the invention, the message 210 may also provide a notification to the pharmacy computer 103 that a service request may be available, perhaps at the printer 184 or facsimile 186.

Having received the barcoded service request, the pharmacist/pharmacy or other healthcare provider may then perform one or more of the requested services, which may include counseling services in accordance with one or more healthcare programs. Examples of these counseling services may include, but are not limited to, one or more of:
- Performing a comprehensive medication review to identify, resolve and prevent medication-related problems, including adverse drug events with the prescribed drug or product to be utilized;
- Motivating a patient to become more adherent to medication therapy;
- Offering a patient advice and actions to support lower out of pocket cost choices under a patient's health benefit;
- Closing a gap in care by adding a medication to the patient's regimen in accordance with clinical guidelines;
- Enrolling a patient in a medication copayment savings program;
- Enrolling a patient in a subscription service delivery via mobile (e.g., cell phone) messaging;
- Providing verbal or printed education and training designed to enhance patient understanding and appropriate use of the prescribed product, as well as to enhance patient understanding of benefits and risks of the prescribed drug or product;
- Obtaining necessary assessments of the patient's health status;
- Formulating a product treatment plan;
- Providing an updated Personal Medication Record (PMR) and Medication Action Plan (MAP) to each patient following each consultation, which may be provided in a data collection field of the barcoded service request;
- Providing information, support services, and resources designed to enhance patient adherence for utilization of the prescribed product;
- Documenting the care delivered;
- Communicating essential information to the patient's primary care providers; and/or
- Referring the patient to an appropriate healthcare provider if necessary.

FIG. 2B illustrates a variation of the block diagram of FIG. 2A. As shown by FIG. 2B, the service provider computer 104 may be comprised of two or more distinct service provider computers 104a and 104b that are in communication with each other. Service provider computer 104a may be operative with the pharmacy computer 103 and/or claims processor computer 106 while service provider computer 104b may be operative with other pharmacy computers and/or claims processors. However, service provider computer 104b may have a data processing arrangement with service provider computer 104a. Under the data processing agreement, the service provider computer 104a may be permitted to utilize or offer services of the service provider computer 104b, including the business rules described above and the service request module 108. Accordingly, the services of the service provider computer 104b, including the service request module 108, may be available to the pharmacy computer 103 via the service provider computers 104a and 104b.

FIG. 5A illustrates an example service request 505 that may be delivered to a recipient via a printer 184 or facsimile 186 in accordance with block 316 of FIG. 3, according to an example embodiment of the invention. As shown in FIG. 5A, the example service request 505 may indicate an opportunity for counseling services to be provided by a pharmacy/pharmacist or other healthcare provider to a patient in accordance with a pharmacy intervention program (PIP). In particular, the example service request may provide the steps that a pharmacist should take to complete a consultation with a patient, including performing adherence consultation using intervention guides and brand-specific patient materials. The example service request 505 may also include data collection fields in the form of a pharmacist signature field and a date field for completion when a pharmacist has delivered the adherence consultation to the patient. It will be appreciated that while FIG. 5A illustrates a counseling opportunity in accordance with a PIP, it can likewise be generalized for counseling opportunities for other healthcare programs, including medication therapy management (MTM) programs or condition/disease management programs.

FIG. 5B illustrates another example service request 525 in accordance with an example embodiment of the invention. However, in addition to indicating an opportunity for counseling services, the example service request 525 may include one or more patient assessment data collection fields. As an example, the patient assessment data collection fields may relate to one or more of the following:

Patient Condition or Health Status
 a. Other drugs or products taken by patient
 b. Identification of patient diseases or conditions
 c. Whether the patient smokes or uses tobacco
Patient understanding regarding the prescribed drug or product
 a. Whether the doctor informed the patient how to take the prescribed drug or product in accordance with guidelines
 b. Whether the patient had a clear understanding of the benefits/risks of the drug or product prior to the consultation
 c. To what extent the patient found the consultation with the pharmacist beneficial (e.g., rate from 1 to 10)
Patient Preferences
 a. Whether the patient believes that a reminder system would help improve his/her adherence
 b. If the patient wishes to receive one or more reminders, the preferred channel of communication (e.g., interactive voice response (IVR), email, text message, letter) along with contact information (e.g., telephone number, email address, mailing address).

It will be appreciated that the data collection fields described above are for illustration purposes, and that many variations are available without departing from example embodiments of the invention.

Figure 5C:

FIG. 5C illustrates another example service request 535 in accordance with an example embodiment of the invention. As shown in FIG. 5C, the example service request 535 may indicate an opportunity for the pharmacy/pharmacist or other healthcare provider to facilitate enrollment of the patient in one or more loyalty programs, including co-pay discount programs. For example, the service request 535 may include a Loyalty ID assigned to a patient for subsequent use. The return of the service request 535 may confirm patient enrollment in the one or more loyalty programs, as well as support any optional billing for the services provided by the pharmacist/pharmacy. However, it will be appreciated that patient enrollments can be facilitated for a variety of other healthcare programs without departing from example embodiments of the invention.

Figure 4:
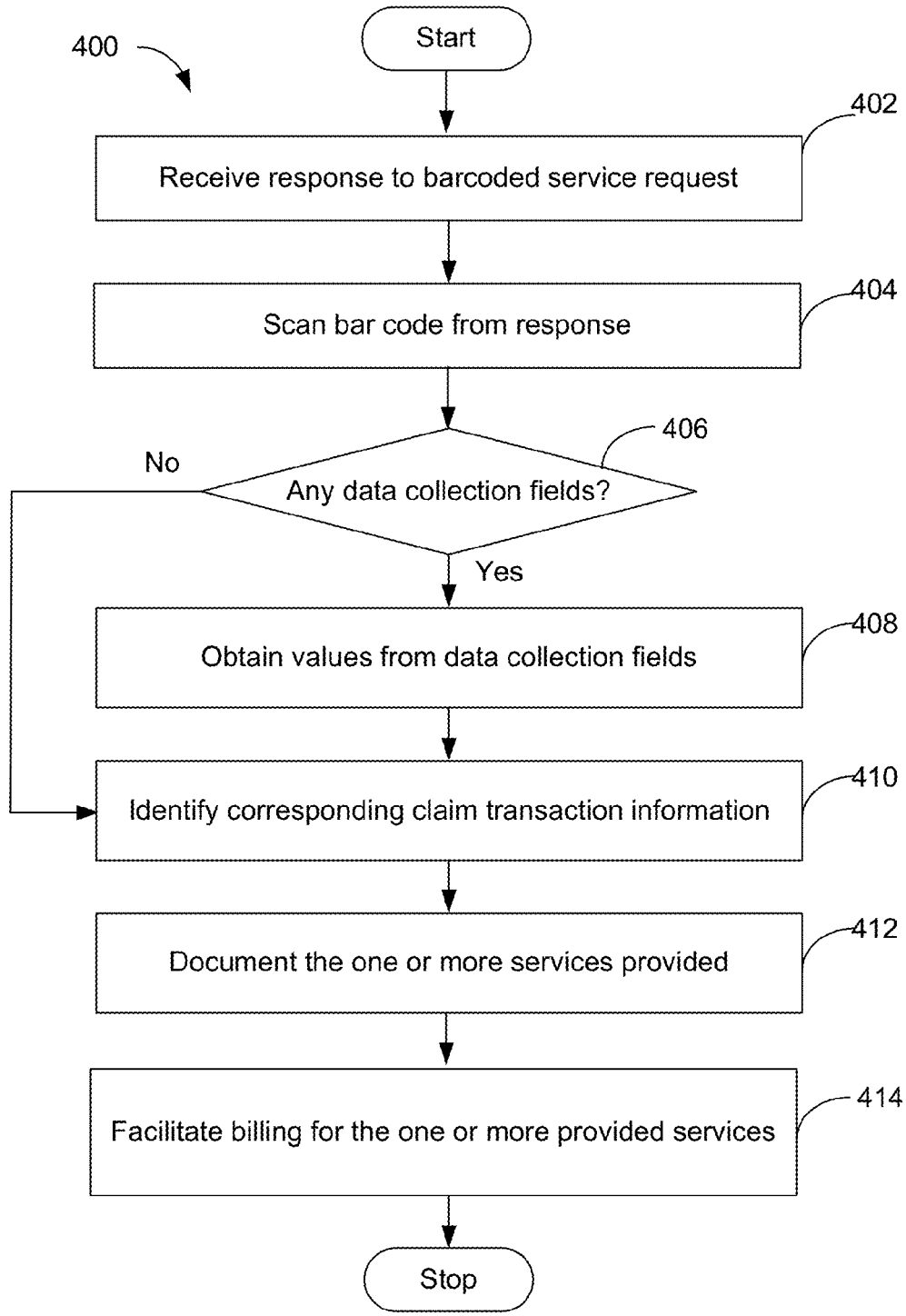
FIG. 4 illustrates an example flow diagram for processing responses to barcoded service requests, according to an example embodiment of the invention.

FIG. 4 illustrates an example flow diagram for processing responses to barcoded service requests, according to an example embodiment of the invention. At block 402, a pharmacist or other healthcare provider may have provided the one or more services, including consultation services, to the patient in accordance with the received barcoded service request. As such, the pharmacist or other healthcare provider may have filled in any data collection fields on the barcoded service request. The pharmacist or other healthcare provider returns a copy of the barcoded service request to the service provider. The copy of the barcoded service request can be returned via facsimile, although other electronic communications can be utilized without departing from example embodiments of the invention. It will be appreciated that even when the copy of the barcoded service request is returned by facsimile, the service provider can receive the copy in an electronic format (e.g., a file). The returned copy of the barcoded service request can serve as a response to the delivered service request. This response may be provided to the service provider computer 104 and/or service request module 108 for further processing at block 404.

At block 404, the service request module 108 and/or service provider computer 104 can scan or otherwise perform optical mark recognition of the bar code in the response to obtain the corresponding bar code information. Block 406 can then determine whether any data collection fields are included with the response. If there are one or more data collection fields, then processing may proceed to block 408, where optical mark recognition, which may include optical character recognition (OCR), can be used to obtain the values from the data collection fields.

At block 410, the bar code information can be used to identify at least a portion of the previously stored prescription transaction information that was associated with the service request. Indeed, the bar code, or information associated with the bar code, may have been previously stored, perhaps in a record in database 182, in conjunction with the prescription transaction information to facilitate later retrieval of the prescription claim information. At block 412, the obtained portion of the prescription transaction information, as well as any obtained values from the data collection fields, can be used in documenting the one or more services provided by the pharmacy to the patient. Likewise, the documentation of the one or more services provided by the pharmacy to the patient can also be used for patient enrollment, either in full or in part, in one or more healthcare programs. For purposes of documentation, one or more of the following example information may be stored in a documentation record:

Patient Identification Information (Name, Cardholder ID)
Patient Contact Information (Address, Email Address, etc.)
Pharmacy/Pharmacist Providing Requested Services to Patient
Date of Provided Services
Values from Data Collection Fields.

It will be appreciated that the above information for the example documentation record has been provided for illustrative purposes only. Accordingly, other information from the prescription claim transaction information, as well as from the response to the barcoded service request, can be included in an example documentation record without departing from example embodiments of the invention.

In addition to documenting services, at block 414, the obtained prescription claim information can also be utilized to facilitate billing for the one or more services provided to the patient by the pharmacy. In an example embodiment of the invention, the billing claim request may be an NCPDP claim request as similarly described herein. As such, the claim request may include a BIN/PCN for a destination claims processor (e.g., provided by service provider computer 104 or claims processor computer 106) for processing the reimbursement for the provided services. The claim request may also indicate the date of service that the services were provided, as well as the pharmacy that provided the services. Upon successful adjudication of the claim request, the pharmacy may be entitled to payment of an amount for providing the requested services. The aggregated payment amounts may be paid to the pharmacy on a periodic basis, according to an example embodiment of the invention.

It will be appreciated that while example embodiments of the invention have illustrated a bar code in a more traditional format, other example embodiments of a bar code may comprise variations of formats of bar codes. For example, bar codes may be provided in a distributed format across a page. Likewise, the bar codes may be provided in a non-traditional graphical format involving various shading or graphical characters or designs without departing from example embodiments of the invention.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general purpose computer, a special-purpose computer, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method, comprising:
   receiving, by a service provider system comprising one or more computers, a prescription claim request from a pharmacy computer associated with a pharmacy, wherein the prescription claim request identifies a patient and a drug or product prescribed for the patient;
   determining, by the service provider system and based at least in part on the drug or product identified in the prescription claim request, that a service request is available, wherein the service request indicates an opportunity for one or more services to be provided to the patient and comprises one or more data collection fields, and wherein the one or more services comprise counseling of the patient in accordance with one or more healthcare programs;
   associating, by the service provider system, a bar code with the service request;
   storing, by the service provider system, prescription claim information in association with the bar code, wherein the prescription claim information comprises information included in the prescription claim request;
   directing, by the service provider system, a delivery of the service request and the associated bar code to the pharmacy;
   receiving, by the service provider system, a response to the service request, wherein the response includes the bar code, and wherein the response comprises one or more values associated with the one or more data collection fields;
   identifying, by the service provider system, the one or more values associated with the one or more data collection fields;
   retrieving, by the service provider system, at least a portion of the prescription claim information based at least in part on the bar code; and
   generating, by the service provider system and based at least in part on the retrieved prescription claim information, documentation information relating to the provision of the one or more services to the patient,
   wherein the documentation information comprises at least one documentation record that identifies the one or more services provided to the patient, the patient, the prescribed drug or product, and the one or more values associated with the one or more data collection fields.

2. The method of claim 1, wherein determining that the service request is available comprises determining that the service request is available based at least in part on at least one of: (i) past prescription claim transaction history associated with the patient, (ii) an age of the patient, (iii) a gender of the patient, (iv) a location associated with the patient, or (v) the pharmacy associated with the prescription claim request.

3. The method of claim 1, wherein the response is a returned copy of the delivered service request.

4. The method of claim 1, wherein the one or more values are identified by utilizing optical mark recognition.

5. The method of claim 1, wherein the one or more healthcare programs comprise at least one of: a pharmacy intervention program, a medication therapy management (MTM) program, or a loyalty program.

6. The method of claim 1, further comprising:
   obtaining, by the service provider system and based at least in part on the bar code included in the response, at least a portion of the prescription claim information associated with the bar code in order to facilitate billing for the one or more services provided to the patient.

7. The method of claim 1, further comprising:
   utilizing, by the service provider system, the documentation information for patient enrollment in one or more additional healthcare programs.

8. The method of claim 1, wherein the service request is sponsored by a pharmaceutical manufacturer for the prescribed drug or product.

9. A system, comprising:
   at least one memory storing computer-executable instructions; and
   at least one processor configured to access the at least one memory and to execute the computer-executable instructions to:
      receive a prescription claim request from a pharmacy computer associated with a pharmacy, wherein the prescription claim request identifies a patient and a drug or product prescribed for the patient;
      determine, based at least in part on the drug or product identified in the prescription claim request, that a service request is available, wherein the service request indicates an opportunity for one or more services to be provided to the patient and comprises one or more data collection fields, and wherein the one or more services comprise counseling of the patient in accordance with one or more healthcare programs;
      associate a bar code with the service request;
      store prescription claim information in association with the bar code, wherein the prescription claim information comprises information included in the prescription claim request;
      direct a delivery of the service request and the associated bar code to the pharmacy;
      facilitate receipt of a response to the service request, wherein the response includes the bar code, and wherein the response comprises one or more values associated with the one or more data collection fields;
      identify the one or more values associated with the one or more data collection fields;

retrieve at least a portion of the prescription claim information based at least in part on the bar code; and generate documentation information relating to the provision of the one or more services to the patient based at least in part on the retrieved prescription claim information, wherein the documentation information comprises at least one documentation record that identifies the one or more services provided to the patient, the patient, the prescribed drug or product, and the one or more values associated with the one or more data collection fields.

10. The system of claim 9, wherein the service request is determined to be available based at least in part on at least one of: (i) past prescription claim transaction history associated with the patient, (ii) an age of the patient, (iii) a gender of the patient, (iv) a location associated with the patient, or (v) the pharmacy associated with the prescription claim request.

11. The system of claim 9, wherein the response is a returned copy of the delivered service request.

12. The system of claim 9, wherein the at least one processor is further configured to execute the computer-executable instructions to:

retrieve, based at least in part on the bar code included in the response, at least a portion of the prescription claim information associated with the bar code in order to facilitate billing for the one or more services provided to the patient.

13. The system of claim 9, wherein the one or more values are identified by utilizing optical mark recognition.

14. The system of claim 9, wherein the one or more healthcare programs comprise at least one of: a pharmacy intervention program, a medication therapy management (MTM) program, or a loyalty program.

* * * * *